(12) United States Patent
Collings et al.

(10) Patent No.: US 7,758,523 B2
(45) Date of Patent: Jul. 20, 2010

(54) REMOTE SENSING SHOE INSERT APPARATUS, METHOD AND SYSTEM

(75) Inventors: Timothy David Collings, Surrey (CA); Joanne Rosalie Younker, Whistler (CA)

(73) Assignee: Kineteks Corporation, Vancouver, BC (CA)

( * ) Notice: Subject to any disclaimer, the term of this patent is extended or adjusted under 35 U.S.C. 154(b) by 96 days.

(21) Appl. No.: 10/853,469

(22) Filed: May 24, 2004

(65) Prior Publication Data

US 2005/0261609 A1 Nov. 24, 2005

(51) Int. Cl.
*A61B 5/11* (2006.01)
(52) U.S. Cl. .......................................... 600/592; 73/172
(58) Field of Classification Search ................. 600/587, 600/592, 595; 73/172; 473/269
See application file for complete search history.

(56) References Cited

U.S. PATENT DOCUMENTS

| | | | |
|---|---|---|---|
| 3,169,022 A | 2/1965 | Kretsinger | |
| 3,352,559 A | 11/1967 | Larsen | |
| 4,037,847 A | 7/1977 | Lorang | |
| 4,703,445 A * | 10/1987 | Dassler | 702/160 |
| 4,745,930 A * | 5/1988 | Confer | 600/592 |
| 4,771,394 A | 9/1988 | Cavanagh | |
| 4,814,661 A * | 3/1989 | Ratzlaff et al. | 310/328 |
| 4,972,503 A * | 11/1990 | Zurlinden | 725/14 |
| 5,118,112 A | 6/1992 | Bregman et al. | |
| 5,282,326 A * | 2/1994 | Schroer et al. | 36/44 |
| 5,285,586 A | 2/1994 | Goldston et al. | |
| 5,373,651 A * | 12/1994 | Wood | 36/114 |
| 5,408,873 A * | 4/1995 | Schmidt et al. | 73/862.625 |
| 5,471,405 A | 11/1995 | Marsh | |
| 5,500,635 A * | 3/1996 | Mott | 340/323 R |
| 5,724,265 A | 3/1998 | Hutchings | |
| 5,779,557 A | 7/1998 | Scannell et al. | |
| 6,059,576 A * | 5/2000 | Brann | 434/247 |
| 6,122,494 A * | 9/2000 | Tuttle | 455/193.1 |
| 6,356,856 B1 | 3/2002 | Damen et al. | |
| 6,360,597 B1 | 3/2002 | Hubbard, Jr. | |
| 6,408,545 B1 | 6/2002 | Song | |
| 6,788,200 B1 * | 9/2004 | Jamel et al. | 340/539.13 |
| 2003/0009308 A1 * | 1/2003 | Kirtley | 702/141 |
| 2004/0123498 A1 * | 7/2004 | Lietzman | 36/145 |

FOREIGN PATENT DOCUMENTS

WO WO 03/045179 A2 6/2003

OTHER PUBLICATIONS http://www.novel.de/;"quality in pressure distribution measurement", Oct. 31, 2003; 1 page.

(Continued)

*Primary Examiner*—Max Hindenburg
*Assistant Examiner*—Renee Danega
(74) *Attorney, Agent, or Firm*—Klarquist Sparkman, LLP

(57) ABSTRACT

A method, apparatus and system for communicating to a remote location a representation of a physical condition caused by a foot. The method involves communicating to a transmitter unit at least partially held within a cavity in a foot support operable to be inserted into footwear, a condition signal representing the physical condition sensed by a condition sensor; and transmitting from the transmitter unit a radio frequency (RF) signal representing the condition signal, for reception by a receiver unit spaced apart from the transmitter unit. An apparatus and system using the method are also disclosed.

61 Claims, 8 Drawing Sheets

OTHER PUBLICATIONS http://www.novel.de/nav1/nav_11.htm; "General Info", Oct. 31, 2003; 2 pages.

http://www.novel.de/nav/nav4/nav_425.htm; "Support". Oct. 31, 2003; 3 pages.

http://www.novel.de; "pedar family brochure", Oct. 31, 2003; 2 pages.

http://www.novel.de/nav2/nav_23.htm; "Product Info", Oct. 31, 2003; 1 page.

http://www.rsscan.com/frame_index.php; "Welcome to . . . Rscan International", Oct. 31, 2003; 1 page.

http://www.rsscan.com/products/footscan_insole.php; "Products footscan insole", Oct. 31, 2003; 1 page.

http://www.rsscan.com/products/footscan_requirements.php; "Products System requirements", Oct. 31, 2003; 1 page.

http://www.rsscan.com/support/publications.php; "Multimedia Publications", Oct. 31, 2003; 3 pages.

http://www.tekscan.com/medical/system_fscan.html; "The F-Scan Clinical System", Oct. 31, 2003; 2 pages.

http://www.tekscan.com/medical/specs_fscan.html; F-Scan Clinical—Specifications & Features, Oct. 31, 2003; 2 pages.

http://www.tekscan.com/technology.html; "Tekscan Technology", Oct. 31, 2003; 7 pages.

Morley et al., "In-Shoe Multisensory Data Acquisition System" (2001) 48:7 IEEE Transactions on Biomedical Engineering 815.

Hsiao et al., "Accuracy and precision of two in-shoe pressure measurement systems" (2002) 45:8 Ergonomics ISSN 537.

Zhu et al., "A Microprocessor-Based Data-Acquisition System for Measuring Plantar Pressures from Ambulatory Subjects" (1991) 38:7 IEEE Transactions on Biomedical Engineering 710.

Smith et al., "Evaluation of Force-Sensing Resistors for Gait Event Detection to Trigger Electrical Stimulation to Improve Walking in the Child With Cerebral Palsy" (2002) 10:1 IEEE Transactions on Neural Systems and Rehabilitation Engineering 22.

Morris et al., "Shoe-integrated sensor system for wireless gait analysis and real-time feedback" (2002) 3 IEEE 2468.

Lawrence et al., "Wireless In-Shoe Force System" (1997) Proceedings—19th International Conference—IEEE/EMBS 2238.

Abu-Faraj et al., "A Holter-Type, Microprocessor-Based, Rehabilitation Instrument for Acquisition and Storage of Plantar Pressure Data" (1997) 34:2 Journal of Rehabilitation Research & Development 187.

Wertsch et al., "A Portable Insole Plantar Pressure Measurement System" (1992) 29:1 Journal of Rehabilitation Research & Development 13.

Lampinen HM, "A comparison between foot pressure measurement systems and their suitability in research and in the treatment of diabetics"; http://www.kirjasto.jypoly.fi/opin/abstract.asp?aidee=525; Oct. 31, 2003; 1 page.

Pollo et al., "Plantar Pressures in Fiberglass Total Contact Casts vs. a New Diabetic Walking Boot" (2003) Baylor University Medical Center 45.

Crenshaw et al., "Plantar Pressures in Short Leg Casts versus a New Diabetic Walking Boot" (no date) Baylor University Medical Center, http://www.indiana.edu/~hperk500/gcma01a/a107cren.pdf.

LaFontaine et al., "Plantar Pressure Distribution Measured During Alpine Ski Turns". Clinical Biomechanics, (1999) 14:8 558.

http://www.isb.ri.ccf.org/biomch-1/archives/biomch-1-1997-06/00166.html.

http://www.isb.ri.ccf.org/biomch-1/archives/biomch-1-2001-12/00009.htmlsportdiscusinsoles.txtl.

Chris Kirtley, "Gait Analysis from the Ground Up", Rehab Management—The Interdisciplinary Journal of Rehabilitation, www.rehabpub.com, Feb. 2001, pp. 1-2, Los Angeles, CA, USA.

Chris Kirtley, "SmartSole", The Catholic University of America—Biomedical Faculty, www.engineering.cua.edu, pp. 1-4, Washington, DC, USA.

\* cited by examiner

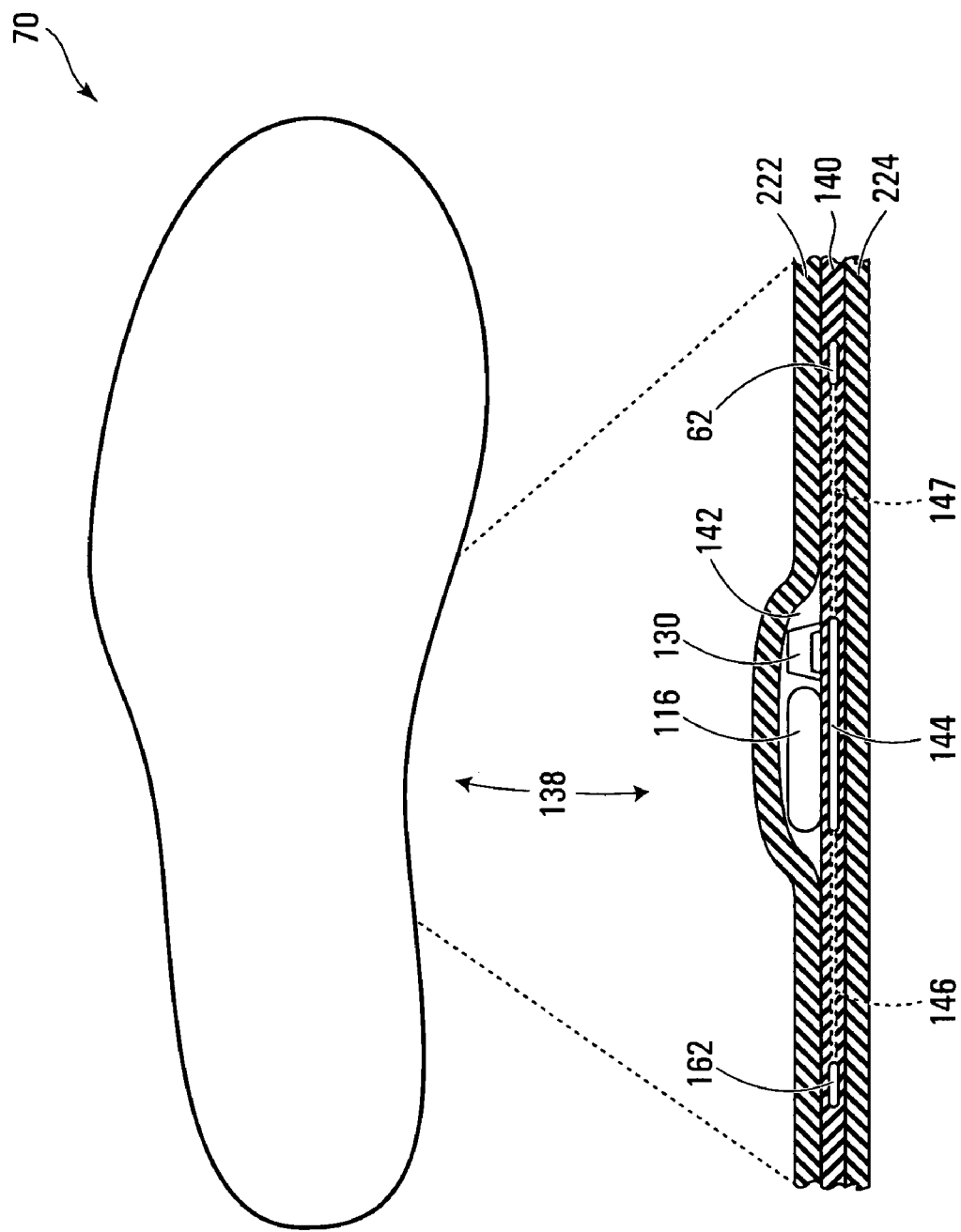

REMOTE SENSING SHOE INSERT APPARATUS, METHOD AND SYSTEM

BACKGROUND OF THE INVENTION

1. Field of Invention

The present invention relates to remote sensing, and more particularly, to an apparatus, method and system for communicating to a remote location a representation of a physical condition caused by a foot.

2. Description of Related Art

In many sports it is Useful to measure and analyse physical conditions caused by a foot in order to improve sports performance. In particular, an analysis of how weight is shifted to different parts of a foot or to the other foot may help to optimize the performance of an athlete in many sports such as golf or baseball.

A number of electronic devices are known for measuring a force caused by a foot, for example, however these devices have various drawbacks. Some devices require custom-built footwear to be constructed in order to measure force caused by the foot, and cannot readily be used with an athlete's existing footwear. Many devices require an inconvenient and unsightly wire connection to a measurement apparatus, which is either obtrusively worn on the body or which must be carried along to a new location every time the athlete moves.

There is therefore a need for an unobtrusive device capable of sensing a physical condition caused by a foot and communicating to a remote location a representation of the physical condition, wherein the device does not necessarily require custom-built footwear. These and other problems in the art are addressed by embodiments of the present invention.

SUMMARY OF THE INVENTION

In accordance with one aspect of the invention, there is provided a method of communicating to a remote location a representation of a physical condition caused by a foot. The method involves communicating to a transmitter unit held within a cavity in a foot support operable to be inserted into footwear, a condition signal representing the physical condition sensed by a condition sensor; and transmitting from the transmitter unit a radio frequency (RF) signal representing the condition signal, for reception by a receiver unit spaced apart from the transmitter unit.

In accordance with another aspect of the invention, there is provided an apparatus for use in sensing a physical condition caused by a foot. The apparatus includes a foot support operable to be inserted into footwear, the foot support having a transmitter unit holder including a cavity operable to hold a transmitter unit operable to receive from a condition sensor a condition signal representing the physical condition. The foot support is formed of a material permitting the transmitter unit to transmit from the transmitter unit holder a radio frequency (RF) signal representing the condition signal, for reception by a receiver unit spaced apart from the transmitter unit.

The foot support may be removably insertable into the footwear.

The foot support may include an arch support portion, the cavity being formed in the arch support portion. The arch support portion may include a wall defining the cavity therein. The wall may include first and second spaced apart wall portions and a third wall portion extending between the first and second wall portions, such that the cavity is generally wedge shaped having a thick portion at a first end of the cavity and tapering to a thin portion at a second end of the cavity. The thick portion of the cavity may be located subjacent a medial longitudinal arch of the foot, and the thin portion of the cavity may be located subjacent a lateral longitudinal arch of the foot when the foot support is inserted in the footwear and the footwear is worn by the foot.

The transmitter unit holder may include a connector operable to cooperate with a complementary connector on the transmitter unit for holding the transmitter unit in the cavity.

The foot support may further include an opening for holding an electrical conductor extending from the cavity to a sensor mount on the foot support.

The foot support may further include a sidewall having an opening, the opening being in communication with the cavity.

The foot support may further include an underlay covering the cavity. The underlay may include a sensor mount for mounting a sensor. The underlay may be operable to extend into a forefoot region of the footwear. The foot support may further include an overlay on the arch support portion, the overlay being operable to extend into a forefoot region of the footwear. The underlay and the overlay may be operable to hold the condition sensor therebetween.

The apparatus may further include a plurality of sensor mounts such that the sensor mounts may be disposed generally symmetrically apart on opposite sides of a longitudinal axis of the foot support. The sensor mounts may be disposed generally symmetrically apart on opposite sides of a transverse axis of the foot support.

The apparatus may further include a condition sensor mounted to the sensor mount, and the condition sensor may include a force sensor.

The arch support portion may have a top portion and a bottom portion and the cavity may be formed in the bottom portion. The bottom portion may include an opening in communication with the cavity.

The foot support may include a heel portion and a sensor mount on the heel portion for mounting the condition sensor. The apparatus may include a sensor mount on the arch support portion for mounting the condition sensor. The foot support may include a forward portion and a sensor mount on the forward portion for mounting the condition sensor. The forward portion may include a first Metatarsophalangeal (MTP) joint support portion for supporting a first joint of a foot, the first MTP joint support portion having a sensor mount for mounting the condition sensor. The forward portion may include a toe portion, which may have a sensor mount for mounting the condition sensor.

In accordance with another aspect of the invention, there is provided an apparatus for communicating to a remote location a representation of a physical condition caused by a foot. The apparatus includes a foot support operable to be inserted into footwear, the foot support having a transmitter unit holder including a cavity operable to hold a transmitter unit. The apparatus further includes a transmitter unit in the transmitter unit holder, the transmitter unit being operable to receive from a condition sensor a condition signal representing the physical condition caused by the foot. The transmitter unit is further operable to transmit from the transmitter unit holder a radio frequency (RF) signal representing the condition signal, for reception by a receiver unit spaced apart from the transmitter unit.

The foot support may be removably insertable into the footwear.

The transmitter unit may further include a memory operable to store a plurality of condition values representing the condition signal, and the transmitter unit may accumulate the condition values in the memory for later transmission by the transmitter unit as the radio frequency (RF) signal.

The transmitter unit may be operable to enter an active state from a low power state in response to the condition signal meeting a first criterion. The transmitter unit may be operable to enter a low power state from an active state in response to the condition signal meeting a second criterion.

The foot support may include a wall defining the cavity therein, the wall including first and second spaced apart wall portions and a third wall portion extending between the first and second wall portions, such that the transmitter unit may be held between the first, second, and third wall portions.

The foot support may further include an arch support portion, the cavity being formed in the arch support portion.

The cavity may have a shape operable to cooperate with a complementary shape of the transmitter unit to facilitate the transmitter unit being held in the cavity. The transmitter unit holder may include a connector operable to cooperate with a complementary connector on the transmitter unit for holding the transmitter unit in the cavity.

The transmitter unit may include a circuit board. The circuit board may further include a radio frequency (RF) circuit mounted on the circuit board and operable to transmit the radio frequency (RF) signal. The circuit board may further include a power source (for example, a battery) mounted on the circuit board and operable to power the radio frequency (RF) circuit. The apparatus may further include a sidewall having an opening, the opening being in communication with the cavity, wherein the battery may be installed from the opening in the sidewall.

The circuit board may further include a signal conditioning circuit mounted on the circuit board and operable to facilitate data acquisition from the condition sensor. The circuit board may further include a sampling circuit operable to sample the condition signal to determine an amplitude of the condition signal at a plurality of times. The circuit board may further include a format converter circuit for converting an output of the sampling circuit into a predetermined format suitable for transmission by the radio frequency (RF) circuit. The predetermined format may include at least one data packet.

The apparatus may further include at least one condition sensor (for example, a force sensor) mounted on the foot support.

The circuit board may further include a receiver circuit operable to receive configuration information from an external source, and the configuration information may include a "wake-up" command operable to cause the transmitter unit to enter into an active state from a dormant state.

The apparatus may further include a receiver unit spaced apart from the transmitter unit and operable to receive from the transmitter unit the radio frequency (RF) signal representing the condition signal.

In accordance with yet another aspect of the invention, there is provided an apparatus for use in sensing a physical condition caused by a foot. The apparatus includes foot support means for supporting a foot, the foot support means being operable to be inserted into footwear and having transmitter unit holding means including a cavity for holding a transmitter unit operable to receive from a condition sensor a condition signal representing the physical condition. The foot support means is formed of a material permitting the transmitter unit to transmit from the transmitter unit holding means a radio frequency (RF) signal representing the condition signal, for reception by a receiver unit spaced apart from the transmitter unit.

In accordance with yet another aspect of the invention, there is provided an apparatus for communicating to a remote location a representation of a physical condition caused by a foot. The apparatus includes foot support means for supporting a foot, the foot support means being operable to be inserted into footwear and having transmitter holding means including a cavity for holding transmitter means. The apparatus further includes transmitter means held by the transmitter holding means, for transmitting a radio frequency (RF) signal, the transmitter means being operable to receive from a condition sensor a condition signal representing the physical condition caused by the foot, and to transmit from the transmitter holding means the radio frequency (RF) signal representing the condition signal, for reception by receiver means spaced apart from the transmitter means.

In accordance with yet another aspect of the invention, there is provided an apparatus for communicating to a remote location a representation of a physical condition caused by a foot acting on a condition sensor. The apparatus includes a foot support operable to be inserted into footwear. The apparatus further includes a transmitter unit formed within an arch area of the foot support, and operable to receive from a condition sensor a condition signal representing the physical condition caused by the foot, the transmitter unit being operable to transmit from the arch area a radio frequency (RF) signal representing the condition signal, for reception by a receiver unit spaced apart from the transmitter unit. The transmitter unit includes a circuit board, on which is mounted a signal conditioning and conversion circuit, a radio frequency (RF) circuit, and a battery. The signal conditioning and conversion circuit is for conditioning and converting the condition signal into a predetermined format representing the condition signal, the predetermined format being suitable for radio frequency (RF) transmission. The radio frequency (RF) circuit is operable to use the predetermined format to transmit the radio frequency (RF) signal. The battery is operable to power the signal conditioning and conversion circuit and the radio frequency (RF) circuit.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 10 is an enlarged partial side sectional view of an apparatus according to a third embodiment of the invention.

DETAILED DESCRIPTION

Figure 1:
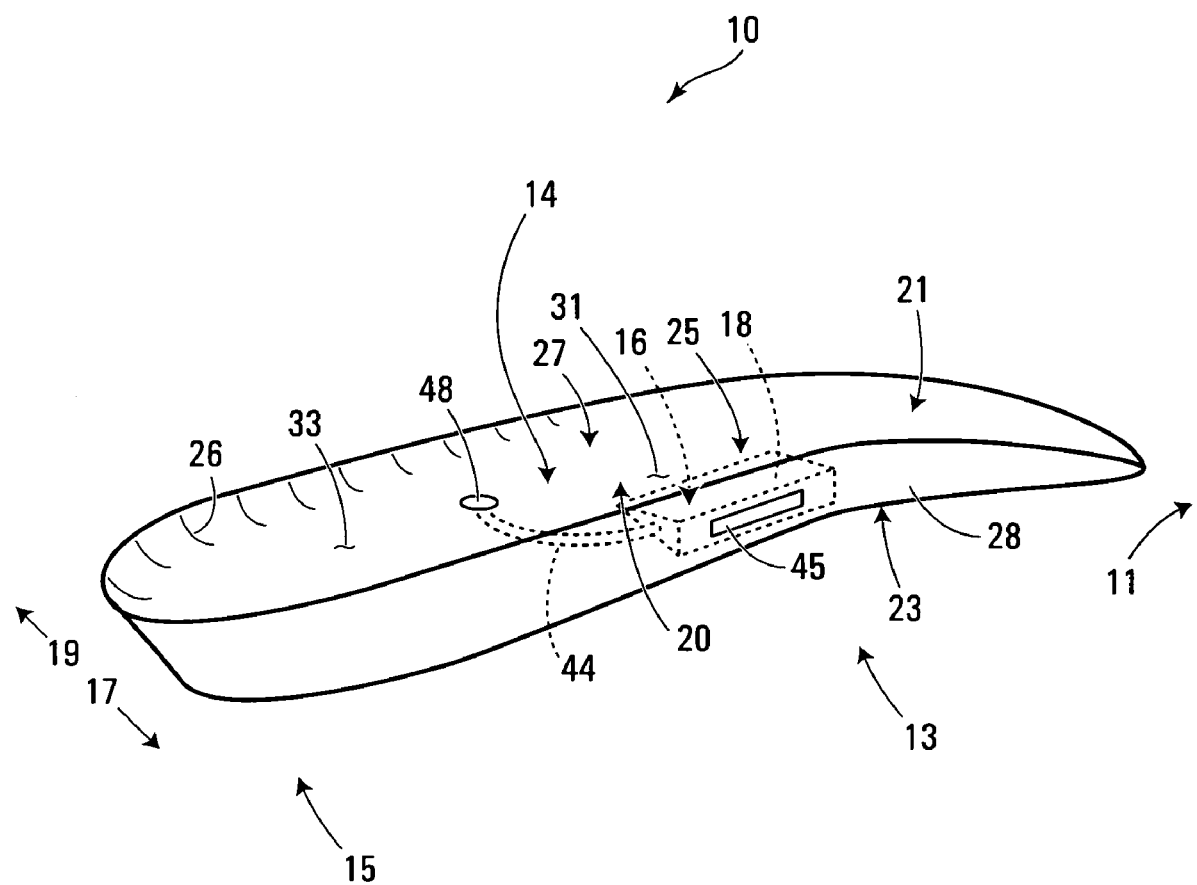
FIG. 1 is a perspective view of an apparatus according to a first embodiment of the invention.

Referring to FIG. 1, an apparatus for use in sensing a physical condition caused by a foot according to a first embodiment of the invention is shown generally at 10. The apparatus 10 may be used in applications such as sports to measure and analyse the physical condition caused by a foot in order to improve sports performance. In particular, the apparatus 10 may be used in golf and other sports where an analysis of how weight is shifted to different parts of a foot or to the other foot is helpful for optimizing performance.

In some implementations, the apparatus 10 may be affixed inside footwear permanently after being inserted therein. However, it is anticipated that many users will wish to retrofit their existing footwear with the present apparatus for temporary use in sensing a physical condition caused by a foot. In the latter case, the apparatus 10 need not be permanently attached to the footwear, but rather is made to be removably insertable into the footwear, so that the apparatus 10 may be inserted by end users into their footwear at will, and similarly removed from their footwear upon completion of use.

In the following description of the apparatus, the terms "forefoot", "midfoot" and "hindfoot" are used to refer to forward, middle and rear/heel portions of a foot, respectively, or to corresponding portions of a foot support or footwear. Thus, in FIG. 1, reference characters 13 and 15 generally indicate midfoot and hindfoot regions of the apparatus 10, respectively. In this embodiment, the apparatus 10 does not extend into a forefoot region of the footwear, however reference character 11 indicates the general location of the forefoot when the apparatus 10 is worn in footwear such as a shoe. Furthermore, the terms "medial" and "lateral" refer to the inside and outside portions of a foot, respectively. The apparatus illustrated in FIG. 1 and in the subsequent figures is specifically designed to be used with a left foot, therefore arrow 17 illustrates a medial direction and arrow 19 illustrates a lateral direction for the "left foot" apparatus illustrated. It will be appreciated that an apparatus for a right foot would generally be a mirror image in shape of the apparatus shown such that the medial and lateral directions (17 and 19) would be effectively reversed. Top and bottom portions are indicated by reference characters 21 and 23 respectively to provide context hereinbelow to references to a top or bottom portion of a component.

The apparatus 10 includes a foot support body 14 operable to support a foot, the body 14 also being operable to be inserted into footwear. The body 14 has a transmitter unit holder (shown generally at 16) including a cavity 18 (shown in broken outline in FIG. 1) operable to hold a transmitter unit (not shown in FIG. 1) operable to receive from a condition sensor a condition signal representing the physical condition. The body 14 is formed of a material permitting a transmitter unit to transmit from the cavity a radio frequency (RF) signal representing the condition signal, for reception by a receiver unit (not-shown in FIG. 1) spaced apart from the transmitter unit.

The body 14 may be an orthotic body shaped from plastic or any other suitable material and is shaped to comfortably support a foot when the body 14 is inserted into footwear such as a shoe or boot, for example. The body 14 includes an arch support portion, shown generally at 20. The arch support portion 20 supports an arch area of a foot, which is an area on the inside of the foot which arches up significantly between the first metatarsophalangeal ("MTP") joint and the heel of the foot, sometimes referred to as a medial longitudinal arch or instep. A medial midfoot portion 25 of the body 14 supports the medial longitudinal arch or instep. A minor arch on the outside of the foot, known as a lateral longitudinal arch, is supported by a lateral midfoot portion 27 of the body 14.

In order to properly fit a foot, the arch support portion 20 of the body 14 is relatively thicker towards the medial side 17 (i.e., inside) of the foot, and gradually slopes downwards towards the lateral side 19 (i.e., outside) of the foot. Furthermore, the arch support portion 20 generally slopes downward in the direction of the forefoot region 11. In some embodiments, the arch support portion 20 may also slope downwards somewhat in the direction of the hindfoot region 15. In the embodiment illustrated, the top surface 33 of the hindfoot region 15 of the body 14 is almost at the same height as the top surface 31 of the thickest portion of the arch support portion 20, albeit the edges of the hindfoot region 15 are curved upwards as indicated by the lines indicating curvature 26. Generally, the body 14 has a top portion 21 and a bottom portion 23, the top portion being adapted to the shape of a foot, and the bottom portion being adapted to the shape of a floor of footwear, which is generally planar in this embodiment.

In the embodiment illustrated, the cavity 18 is formed in the arch support portion 20, and more particularly, in the bottom portion 23 thereof. It may be desirable to maximize the volume of the cavity 18 in order to maximize the room available for a transmitter unit held therein, and this may be accomplished by taking advantage of the specific shape of the arch support portion 20. As noted above, the arch support portion 20 is thicker in the medial direction 17, and thinner in the lateral direction 19, therefore increased capacity may be achieved by forming the cavity 18 to have a thick portion 38 in the medial midfoot portion 25 and tapering to a thin portion 40 in the lateral midfoot portion 27, such that the cavity is generally wedge-shaped. Effectively, when this embodiment of the apparatus 10 is used in footwear worn by a foot, the thick portion 38 of the cavity 18 is located subjacent a medial longitudinal arch of the foot, and the thin portion 40 of the cavity 18 is located subjacent a lateral longitudinal arch of the foot.

Figure 2:
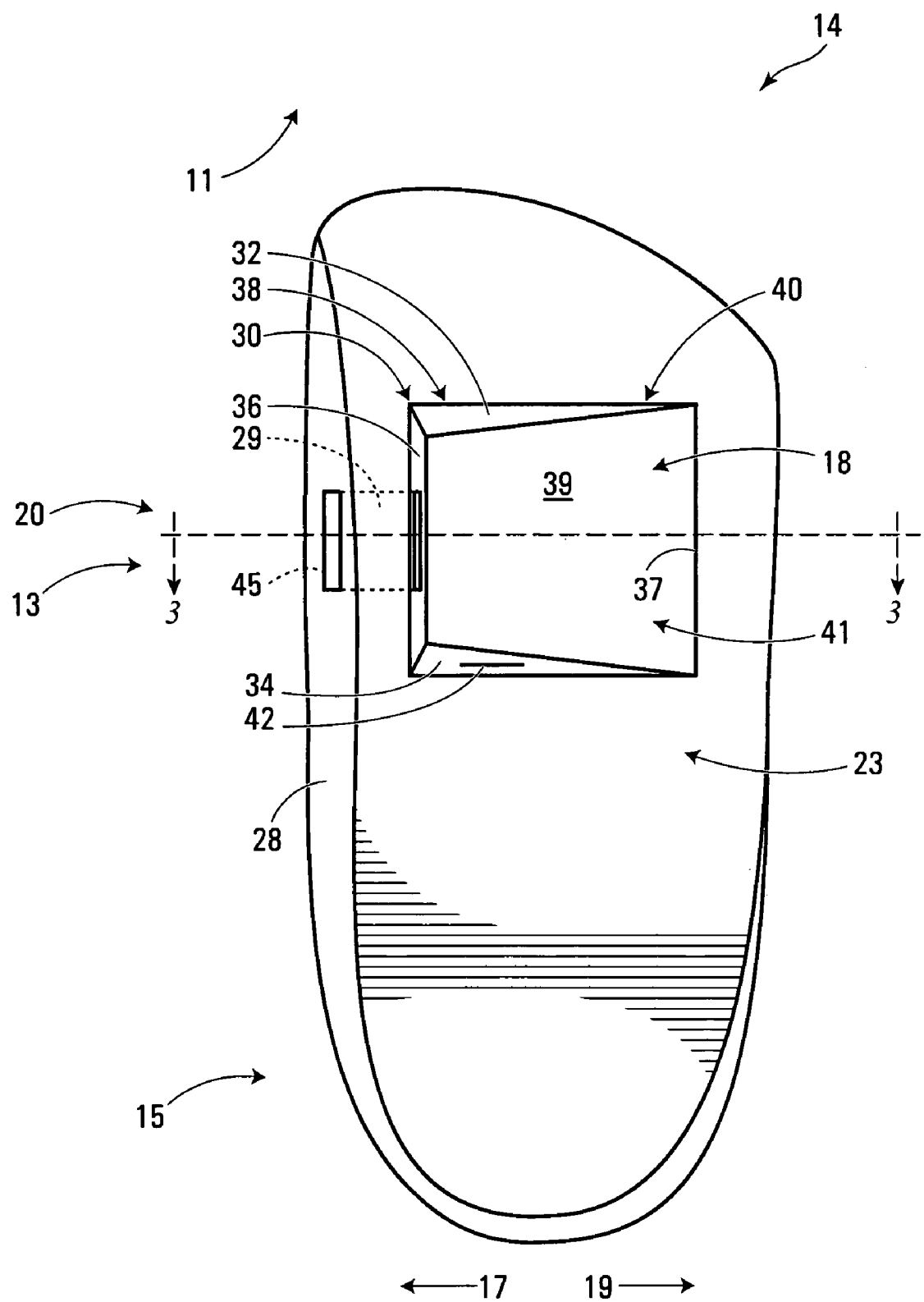
FIG. 2 is a bottom view of the apparatus of FIG. 1.
Figure 3:
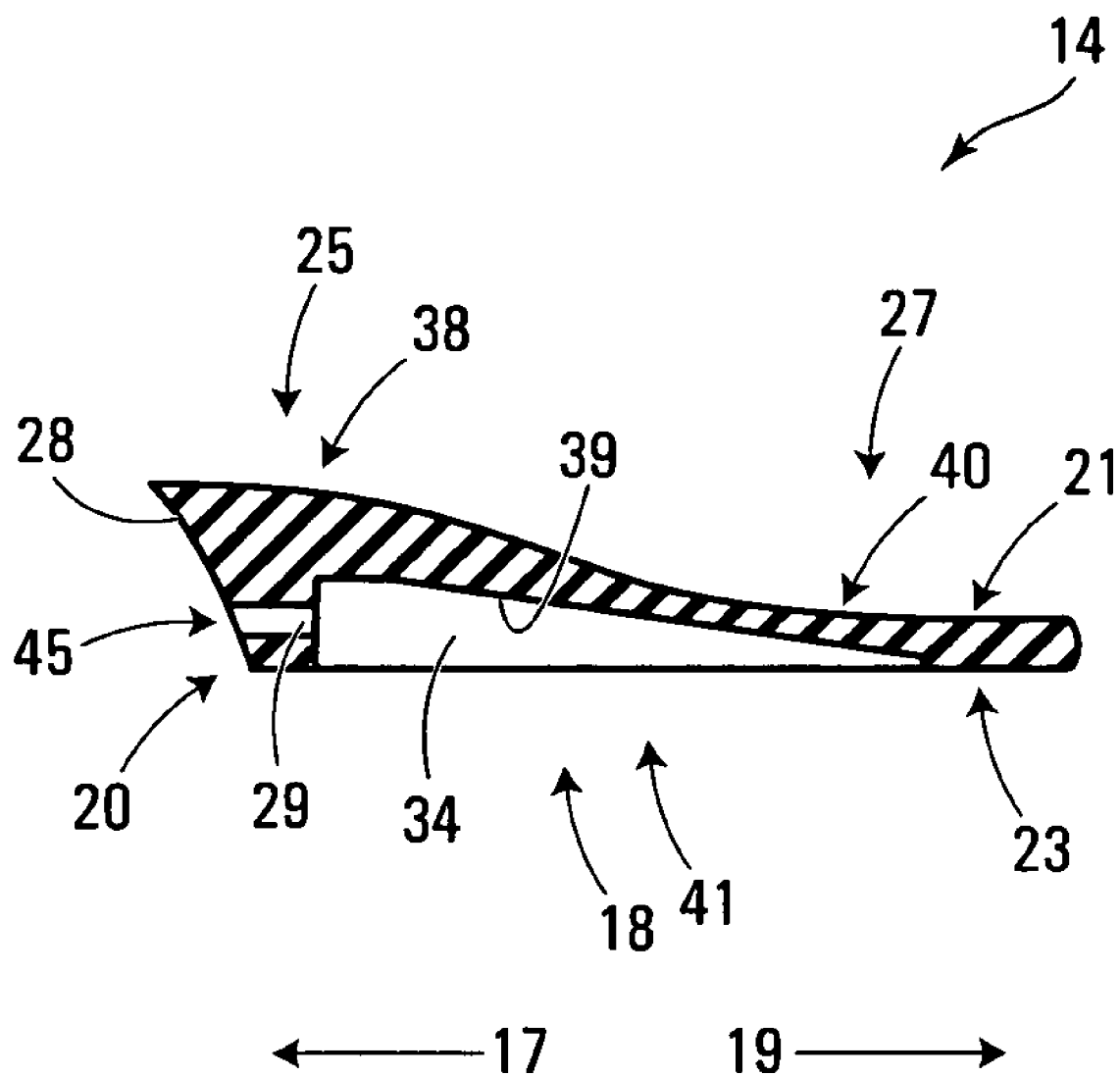
FIG. 3 is a cross-sectional view of the apparatus in FIG. 2 taken along lines 3-3 and looking in a hindfoot direction.

In this embodiment, the cavity 18 spans most of the width of the midfoot portion 13 by extending from the medial midfoot portion 25 across to the lateral midfoot portion 27 (as best seen in FIGS. 2 and 3). However, in another embodiment, the cavity 18 may extend in a lateral direction 19 from the medial midfoot portion 25 to about half way across the midfoot portion 13, or it may extend from the medial midfoot portion 25 to less than half way across the midfoot portion 13.

The body 14 may include an opening 44 for holding an electrical conductor extending from the cavity 18 to a sensor mount 48 on the body 14. FIG. 1 illustrates only one opening 44 and one sensor mount 48, however, it will be appreciated that other embodiments of the invention may include a plurality of openings operable to hold a plurality of respective electrical conductors extending from the cavity 18 to a plurality of respective sensor mounts on the body 14 in order to convey condition signals from respective condition sensors mounted on the sensor mounts to the cavity 18.

Referring to FIGS. 2 and 3, the arch support portion 20 includes a wall shown generally at 30 defining the cavity 18 therein. The wall 30 includes first and second spaced apart wall portions 32 and 34, respectively, and a third wall portion 36 extending between the first and second wall portions 32 and 34. First and second wall portions 32 and 34 are tallest where they intersect the third wall portion 36, and the first and second wall portions 32 and 34 gradually taper as they approach a fourth wall portion 37, spaced apart from the third wall portion 36. A fifth wall portion 39 has a generally planar surface, and cooperates with the first, second, third and fourth wall portions 32, 34, 36, 37 so as to form the cavity 18 in a bottom portion 23 of the body 14 and to define a cavity opening 41 in the bottom portion. The body 14 further includes a sidewall 28 having an opening 45 including a passageway 29 on the medial side 17 of the body 14, the opening 45 being in communication with the cavity 18 through the passageway 29. The opening 45 is operable to allow a power source such as a battery (116 in FIGS. 5 or 6) to be inserted into the cavity 18.

In this embodiment, the transmitter unit (102 in FIG. 6) is form-fitted into the cavity 18 such that it is frictionally held therein. In other embodiments, the transmitter unit holder 16 may include a connector 42 operable to cooperate with a complementary connector (43 in FIG. 6) on a transmitter unit (102 in FIG. 6) for holding the transmitter unit in the cavity 18.

Second Embodiment

Figure 4:
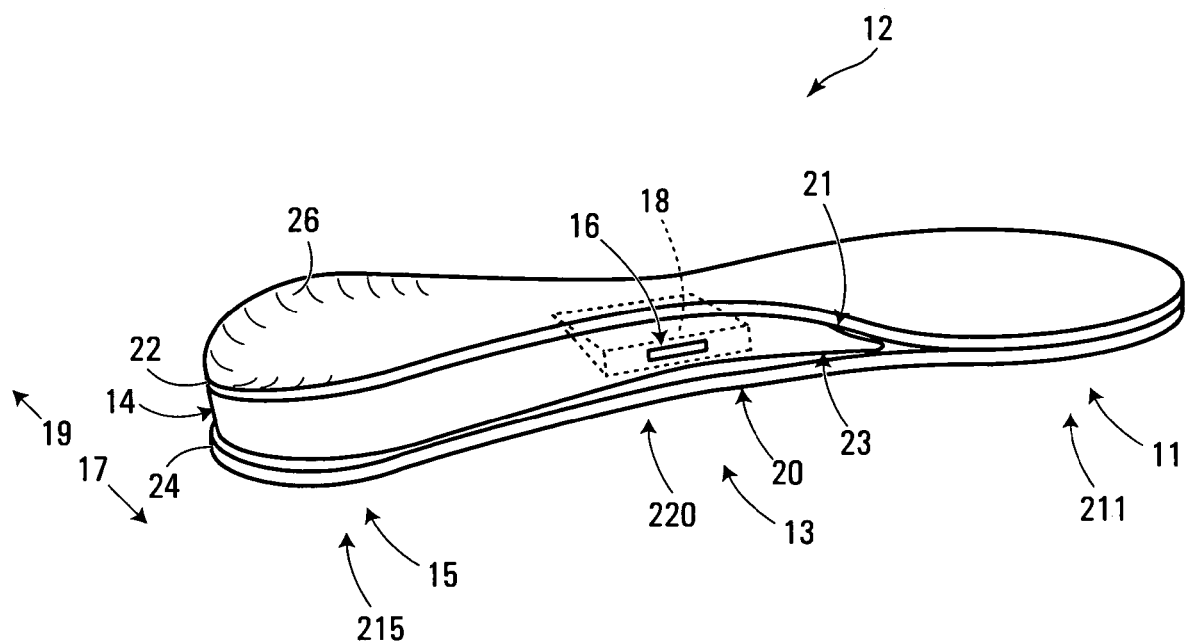
FIG. 4 is a perspective view of an apparatus according to a second embodiment of the invention.
Figure 5:
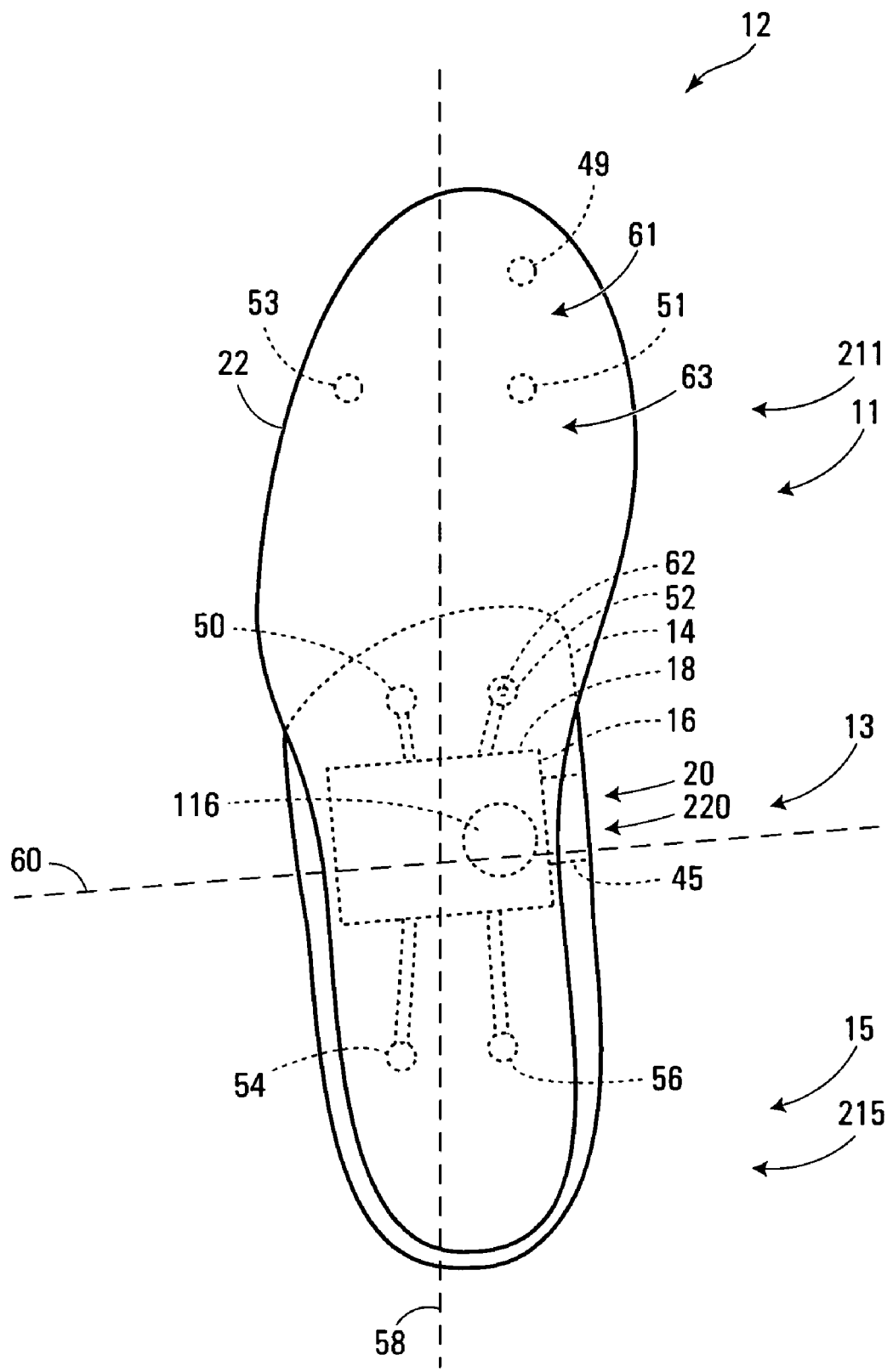
FIG. 5 is a top view of the apparatus of FIG. 4.

Referring now to FIGS. 4 and 5, an apparatus for use in sensing a physical condition caused by a foot according to a second embodiment of the invention is shown generally at 12. The apparatus 12 includes the foot support body 14 previously described, however in this embodiment the body 14 is placed with its bottom portion 23 on an underlay 24 and an overlay 22 is placed on the top portion 21 of the body 14. Effectively, the body 14 is placed in between the overlay 22 and the underlay 24. As previously described, the body 14 has a transmitter unit holder 16 including a cavity 18 (shown in broken outline in FIG. 1) operable to hold a transmitter unit (not shown in FIG. 4, but referred to in FIGS. 6, 7 and 9 by reference character 102). In this embodiment, the apparatus 12 may be affixed inside footwear permanently, or it may be removably insertable into the footwear.

The overlay 22 extends into a forefoot region 11 of the footwear (not shown). In this embodiment, the overlay 22 includes a thin layer of flexible vinyl material operable to protect components of the apparatus 12 underneath it. The overlay is cut to have a size and shape complementary to the footwear for which the apparatus 12 is designed. The apparatus 12 further includes an underlay 24 covering the cavity 18, or more specifically, covering the cavity opening (41 in FIG. 3) in the bottom portion 23 of the body 14. In this embodiment, the underlay 24 extends into the forefoot region 11 of the footwear, and may be joined to the overlay such as by glue, for example. The underlay 24, in this embodiment, includes a thin mat made of resilient foam which is cut to match the size and shape of the footwear for which the apparatus 12 is designed. The shapes of the overlay 22 and underlay 24 are roughly coterminous, as is illustrated in FIGS. 4 and 5. The overlay 22 and 24 underlay may be operable to hold a condition sensor therebetween.

Referring to FIG. 5, the apparatus 12 includes a plurality of sensor mounts 49, 50, 51, 52, 53, 54, 56, which may be as simple as areas to which sensors may be glued, for example. The sensor mounts (for example, 50, 52, 54, 56) may be disposed generally symmetrically apart on opposite sides of a longitudinal axis 58 of the apparatus 12. The sensor mounts 50, 52, 54, 56 may also be disposed generally symmetrically apart on opposite sides of a transverse axis 60 of the apparatus 12.

Sensor mounts for mounting a condition sensor may be located in various other regions of the apparatus 12 as well. Referring to FIG. 5, a sensor mount may be located on a toe portion 61 of the underlay (24), as illustrated by reference character 49, for example. A heel portion 215 of the apparatus 12 may have a sensor mount as shown at 56. A sensor mount, for example, 52, may be located on an arch support portion 220 of the apparatus 12. A sensor mount may be located on a forward portion 211 of the apparatus 12. The forward portion 211 may include a first MTP joint support portion 63 for supporting a first Metatarsophalangeal joint of a foot, and the first MTP joint support portion 63 may have a sensor mount 51. From the foregoing, a person skilled in the art will appreciate that there may be other desirable positions for sensor mounts on the apparatus depending on the application. It has been found through experiment that a suitable layout of sensors in this embodiment includes a sensor under the big toe, a sensor under the 3rd/4th toes, a sensor under each of three metatarsophalangeal joints a sensor in the midfoot region 13, and also two sensors under the heel in the hindfoot region 15 disposed generally symmetrically about the longitudinal axis 58.

Condition sensors 62 may be mounted to one or more of the aforesaid sensor mounts. In this embodiment, the condition sensors 62 may include a force sensitive resistor (FSR Model 400 made by Interlink Electronics of Camarillo, Calif., USA). Alternatively, the condition sensors may include a force sensitive capacitor, for example. (The apparatus 12 may be sold with or without condition sensors mounted at the various sensor mount positions.)

Regardless of how many condition sensors are used, in the embodiments shown, wires from the condition sensors are routed into the cavity 18 for connection to a transmitter unit such as shown at 102 installed therein. In the embodiment shown, the transmitter unit 102 includes a circuit board 110 (shown in FIG. 6), complementary in size and shape to the cavity 18, on which components that make up the transmitter unit are mounted. The components mounted on the circuit board 110 cooperate to form functional blocks as shown in FIG. 7.

Figure 6:
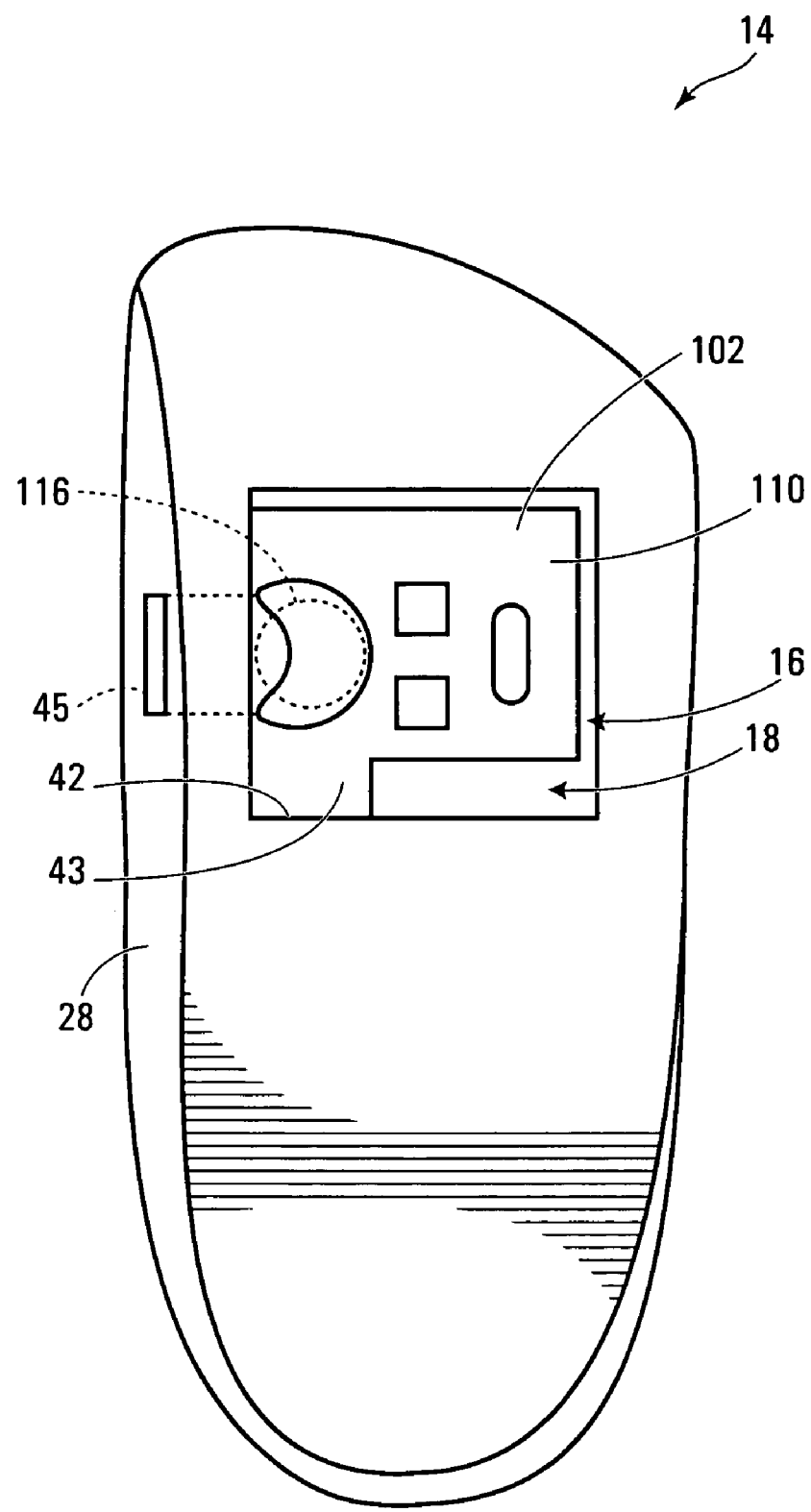
FIG. 6 is a bottom view of an apparatus assembly in which a transmitter unit is held in a cavity of the apparatus of FIG. 1.
Figure 7:
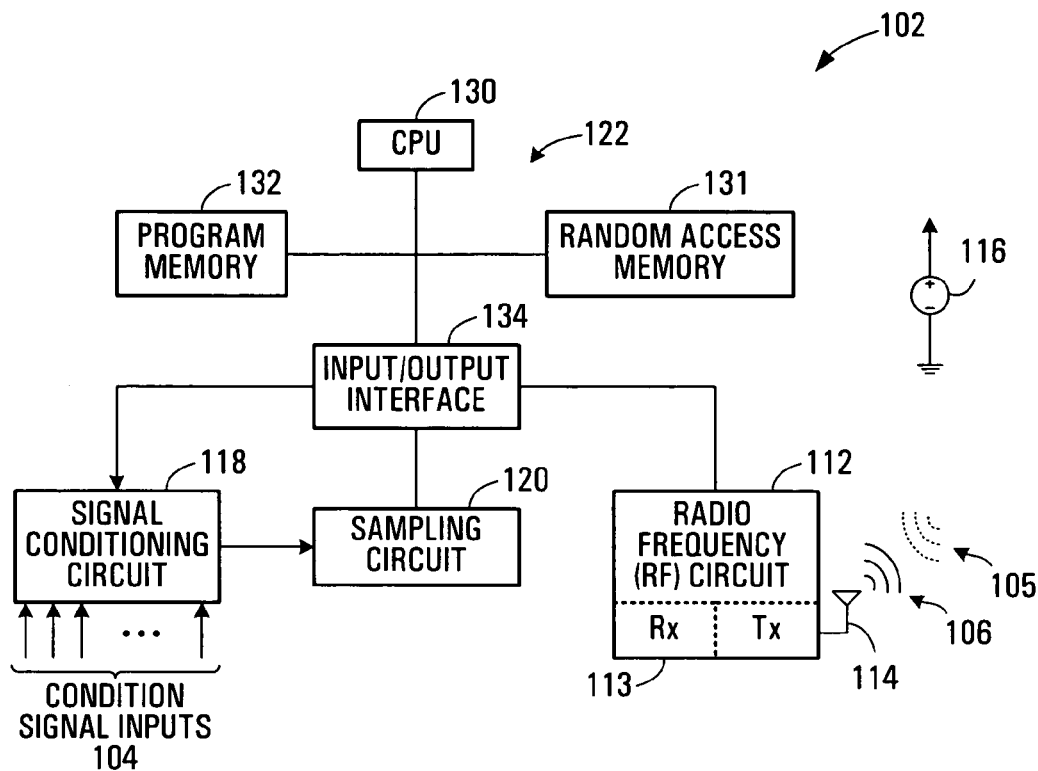
FIG. 7 is a functional block diagram of the transmitter unit of FIG. 6.
Figure 8:
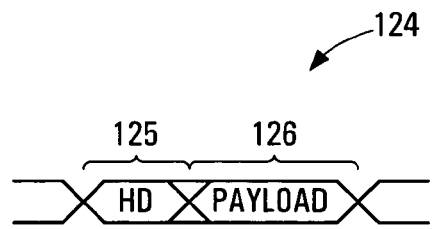
FIG. 8 is a schematic representation of a data packet transmitted or received in the system of FIG. 9.

In this regard, referring to FIG. 7, the transmitter unit 102 includes a radio frequency (RF) circuit 112 operable to transmit from an antenna 114 in the cavity 18 (of FIGS. 1-6 for example) a radio frequency (RF) signal 106 representing the conditions measured by the condition sensors. The transmitter unit 102 further includes a signal conditioning circuit 118 operable to facilitate data acquisition from the condition sensors and having inputs 104 to which are connected respective conductors from the condition sensors. The signal conditioning circuit conditions condition signals received at inputs 104 to produce conditioned signals in a form that is usable by the other functional blocks of the transmitter unit 102. In this embodiment, the signal conditioning circuit 118 may include an operational amplifier circuit (such as the TLV2762, manufactured by Texas Instruments) for scaling voltages of condition signals received from the sensors and for signal buffering. The transmitter unit 102 further includes a sampling circuit 120 operable to sample one or more of the conditioned signals to determine instantaneous amplitudes of the conditioned signals at a plurality of times. Also included is a format converter shown generally at 122 for converting an output of the sampling circuit 120 into a predetermined format suitable for transmission by the radio frequency (RF) circuit 112. In this embodiment, the predetermined format comprises one or more data packets as shown at 124 in FIG. 8, which are inserted into the radio frequency (RF) signal 106 produced by the transmitter unit 102. Referring to FIG. 8, a suitable data packet format may include a header portion 125 for identifying the packet and a payload portion 126 for carrying data representing signal amplitude of the condition signal produced by one or more condition sensors.

In this embodiment, as shown in FIG. 7, the format converter 122 includes a computer comprised of a processor circuit 130 (such as a microprocessor, microcontroller or other programmable digital logic device); a random access memory 131 operable to have variables and data written to and read from it; and an I/O (input/output) interface 134 operable to allow the processor circuit 130 to communicate with and control the signal conditioning circuit 118, the sampling circuit 120 and the radio frequency (RF) circuit 112 in accordance with instructions encoded in a program memory 132 in communication with the processor circuit 130. Some microcontrollers (such as the rfPIC12F675 from Microchip Technology Inc., for example) may integrate much of this functionality into a single integrated circuit.

All of the components of the transmitter unit 102 are powered by a power source 116 such as a battery, which in this embodiment is removably mounted on the circuit board 110 shown in FIG. 6. The circuit board 110 and cavity 18 are configured to position the power source 116 adjacent the opening (45 in FIG. 1) to permit the power source to be removed and replaced as necessary without requiring direct access to the cavity 18 through the underside of the foot support body 14.

Effectively, the transmitter unit 102 in the cavity 18 is operable to receive from at least one condition sensor (62), one or more condition signals (via inputs 104) representing a physical condition caused by a foot, and the transmitter unit is operable to transmit from the cavity a radio frequency (RF) signal 106 representing the condition signals, for reception by a receiver unit 108 spaced apart from the transmitter unit.

More particularly, the instructions encoded in the program memory 132 direct the processor circuit 130 to control the I/O interface 134 to cause a representation of one or more condition signals received from the condition sensors to be transmitted in real time to a receiver. In an alternative operating mode, the random access memory 131 of the transmitter unit 102 may be used to store a plurality of condition values representing the one or more condition signals, such that over a period of time the transmitter unit can accumulate a plurality of condition values in the random access memory 131 for later or periodic transmission, as a data block for example. Effectively, this operating mode implements "data logging", i.e., storing condition sensor information until such time as it can be downloaded to the receiver unit 108. This feature may be useful if it is desired to temporarily use the apparatus 10 when its transmitter unit 102 is out of communication range with the receiver unit 108. The instructions encoded in the program memory 132 may also direct the processor circuit 130 to control the I/O interface 134 to cause the RF circuit 112 to transmit the stored condition values to the receiver unit 108 in response to a download signal received from an external source. The external source may include a switch mounted on the apparatus which, when actuated, causes the download signal to be communicated to the processor circuit 130 through the I/O interface 134. Alternatively, the external source may include an external transmitter unit (which may be part of the receiver unit 108 in some embodiments) operable to communicate a download command embedded in the RF signal 105 (described below), to the processor circuit 130.

To facilitate the conservation of power drawn from the power source 116, the transmitter unit 102 may have a dormant or low power state in which it is not acquiring and transmitting data and may have an active state in which it is acquiring and transmitting data. The transmitter unit 102 may enter into the dormant or low power state when the conditions sensed on one or more condition sensors meet a first criterion such as a voltage lower than an activation threshold. Conversely, the transmitter unit 102 may enter into the active state when the conditions sensed meet a second criterion such as a voltage higher than the activation threshold, which may be defined as a minimum force sensed at one or more force sensors, for example.

Figure 9:
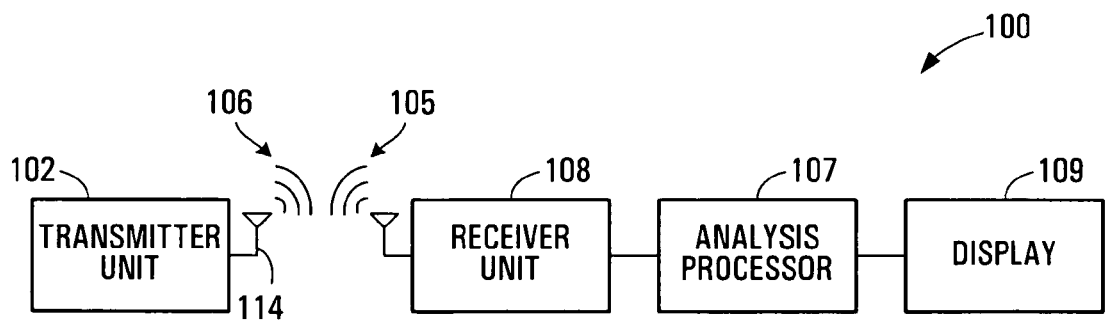
FIG. 9 is a system incorporating the apparatus of FIG. 1 and the transmitter unit of FIG. 6, for analysing a foot condition.

Referring to FIG. 6, the aforementioned foot support body 14 and transmitter unit 102 act as a system for communicating to a remote location a representation of a physical condition caused by a foot. (Foot pressure and temperature are examples of such physical conditions). Referring to FIG. 9, the system shown in FIG. 6 may be part of a larger system 100 for analysing the physical condition caused by a foot. In this embodiment, the system 100 further includes a receiver unit 108, an analysis processor 107 and a display 109. The receiver unit 108 is operable to receive and forward data received from the transmitter unit 102 to the analysis processor 107, which is operable to create a representation of the physical condition caused by a foot on the display 109, or to store a representation of the physical condition at the analysis processor 107 itself.

Referring to FIGS. 7 and 9, in an alternative embodiment the transmitter unit 102 may further include a receiver circuit 113 operable to receive a radio frequency (RF) signal 105 from an external source, which in this embodiment may be the receiver unit 108. The receiver circuit 113 may be part of the radio frequency (RF) circuit 112, for example. The signal 105 may have configuration information which may include a "wake up" command operable to cause the transmitter unit 102 to enter into an active state (in which it is acquiring and transmitting data) from a dormant state or low power state (in which it is not acquiring and transmitting data). The transmitter unit 102 and receiver unit 108 may thus communicate bi-directionally, and such communications may employ data packets as shown in FIG. 8 in both directions, for example.

Third Embodiment

Referring now to FIG. 10, an apparatus for use in sensing a physical condition caused by a foot according to a third embodiment of the invention is shown generally at 70. The apparatus 70 is similar to the apparatus shown in the embodiments described previously, however, in this embodiment, the electronic circuitry and condition sensors may be embedded within an integrated flexible circuit layer 140, which may be manufactured using a synthetic film substrate such as Mylar®, for example. Effectively, the flexible circuit layer 140 performs substantially the same function as the circuit board 110 previously described, thus it may be understood for purposes of this description as a flexible type of circuit board.

FIG. 10 illustrates that in this embodiment the flexible circuit layer 140 is embedded between an overlay 222 and an underlay 224 in order to protect the circuit layer 140 from damage and to enable the apparatus 70 to comfortably support a foot. The overlay 222 and an underlay 224 may be composed of soft rubber, foam, or any other suitable material that would permit a transmitter unit embedded therein (as described below) to transmit a radio frequency (RF) signal to a spaced apart receiver unit. The apparatus 70 may be inserted into and affixed inside footwear permanently, or it may be removably insertable into the footwear.

Although any number of condition sensors may be used, in FIG. 10 only two exemplary embedded condition sensors 62 and 162 are shown. The condition sensors 62 and 162 are connected via first and second embedded conductors 146 and 147, respectively, to embedded circuitry 144 which may include the transmitter unit 102 functionality described above for other embodiments. The condition sensors 62 and 162 are operable to produce respective condition signals which are communicated via the first and second embedded conductors 146 and 147 to the embedded circuitry 144. It will be appreciated that the integrated configuration of this embodiment has the effect of simplifying the task of electrically connecting the sensors to the other circuitry—obviating the use of mechanical connectors or solder joints, for example. However, if desired, it is still possible to mount additional sensors on the flexible circuit layer 140 and to interconnect these sensors using conventional methods to the embedded circuitry 144.

In this embodiment, the power source 116 (battery) and the processor circuit 130 are mounted on the flexible circuit layer 140 within a cavity 142 defined by the overlay 222 as shown. The cavity 142 is preferably disposed in an arch support portion 138 of this embodiment so as to be located subjacent a medial longitudinal arch of the foot (not shown) when the apparatus 70 is used in footwear. The apparatus 70 may be injection-moulded such that the cavity 142 formed is complementary in shape to the volume occupied by mounted components (116 and 130, for example). The embedded circuitry 144, which may include at least part of the circuitry of the transmitter unit 102 in this embodiment, may be disposed in an irregularly-shaped localised area of the flexible circuit layer 140 or it may be distributed throughout the flexible circuit layer 140 as appropriate. The flexible circuit layer 140, need not be coextensive or coterminous with the overlay 222 and underlay 224, which may merge in areas of the apparatus 70 not containing the flexible circuit layer 140.

Effectively, in the apparatus 70, a transmitter unit (102 in FIG. 9) is held in a transmitter unit holder which, in this embodiment, includes both the flexible circuit layer 140 and the cavity 142. The transmitter unit 102 is operable to receive from a condition sensor (62 or 162, for example) a condition signal representing a physical condition caused by the foot. The transmitter unit 102 is further operable to transmit from the transmitter unit holder a radio frequency (RF) signal representing the condition signal, for reception by a receiver (such as receiver unit 109 in FIG. 9) spaced apart from the transmitter unit 102.

In the above embodiments, respective left and right foot transmitter units may transmit on different RF frequencies to the receiver unit 109 so that there is no need for collision detection or synchronization between them.

While specific embodiments of the invention have been described and illustrated, such embodiments should be considered illustrative of the invention only and not as limiting the invention as construed in accordance with the accompanying claims.

What is claimed is:

1. A method of communicating to a remote location a representation of a physical condition caused by a foot, the method comprising:
   installing a battery through an opening in a foot support operable to be inserted into footwear such that the battery is removably received in a cavity in said foot support and in communication with said opening;
   communicating a condition signal representing the physical condition sensed by a condition sensor to a transmitter unit held within said cavity, said transmitter unit being powered by said battery; and
   transmitting from said transmitter unit a radio frequency signal representing said condition signal, for reception by a receiver unit spaced apart from said transmitter unit;
   wherein said cavity has an increasing thickness between a lateral side of said foot support and a medial side of said foot support, the thickest portion of said cavity being subjacent a medial longitudinal arch of the foot when said foot support is worn by the foot in said footwear, said thickness defined as being along a direction which is perpendicular both to a longitudinal axis and a transverse axis of said foot support.

2. The method of claim 1 wherein the cavity has a relatively thick portion in a medial midfoot portion of the foot support and tapers to a thin portion in a lateral midfoot portion of the foot support, such that the cavity is generally wedge-shaped.

3. The method of claim 1 wherein installing the battery further comprises receiving the battery in a first portion of the cavity configured to be subjacent said medial longitudinal arch of the foot when said foot support is used in said footwear.

4. The method of claim 3 wherein receiving the battery further comprises receiving the battery in said first portion of the cavity at a location adjacent said opening.

5. The method of claim 1 wherein said transmitter unit has a shape generally complementary to that of said cavity, said transmitter unit occupying said increasing thickness of said cavity between said lateral side of said foot support and said medial side of said foot support.

6. An apparatus for communicating to a remote location a representation of a physical condition caused by a foot, the apparatus comprising:
   a foot support operable to be inserted into footwear, said foot support having a transmitter unit holder including a cavity operable to hold a transmitter unit, and said foot support having an opening in communication with said cavity for removably receiving a battery for powering said transmitter unit; and
   a transmitter unit in said transmitter unit holder and operable to receive from a condition sensor a condition signal representing the physical condition caused by the foot, said transmitter unit being operable to transmit from said transmitter unit holder a radio frequency signal representing said condition signal, for reception by a receiver unit spaced apart from said transmitter unit;
   wherein said foot support comprises an arch support portion;
   wherein the foot support has a medial side and a lateral side, wherein the foot support has a longitudinal axis and a transverse axis, and wherein the cavity has a tapering thickness, being relatively thicker toward said medial side and relatively thinner toward said lateral side, the thickest portion of said cavity being formed in said arch support portion, wherein said thickness is measured along a direction perpendicular to both said longitudinal and said transverse axes.

7. The apparatus of claim 6 wherein said cavity is generally wedge shaped having a thick portion at a first end of said cavity and tapering to a thin portion at a second end of said cavity.

8. The apparatus of claim 7 wherein said thick portion of said cavity is configured to be located subjacent a medial longitudinal arch of the foot, and wherein said thin portion of said cavity is configured to be located subjacent a lateral longitudinal arch of the foot when said foot support is inserted in said footwear and said footwear is worn by said foot.

9. The apparatus of claim 7 wherein said first end of said cavity is located in a medial midfoot portion of said foot support and said second end of said cavity is located less than about half way across to a lateral midfoot portion of said foot support.

10. The apparatus of claim 6 wherein said foot support includes an electrical conductor extending from said cavity to a sensor mount on said foot support.

11. The apparatus of claim 6 wherein said foot support further comprises an underlay covering said cavity.

12. The apparatus of claim 11 further comprising an overlay on said arch support portion, said underlay and said overlay being operable to extend into a forefoot region of said footwear and to hold said condition sensor therebetween.

13. The apparatus of claim 6 further comprising a plurality of sensor mounts such that said sensor mounts are disposed generally symmetrically apart on opposite sides of said longitudinal axis of said foot support.

14. The apparatus of claim 6 further comprising a plurality of sensor mounts such that said sensor mounts are disposed generally symmetrically apart on opposite sides of said transverse axis of said foot support.

15. The apparatus of claim 6 wherein said arch support portion includes said opening in communication with said cavity.

16. The apparatus of claim 6 wherein said foot support is removably insertable into said footwear.

17. The apparatus of claim 6 wherein said transmitter unit further comprises a memory operable to store a plurality of condition values representing said condition signal, and wherein said transmitter unit accumulates said condition values in said memory for later transmission by said transmitter unit as said radio frequency signal.

18. The apparatus of claim 6 wherein said transmitter unit is operable to enter an active state from a low power state in response to said condition signal meeting a first criterion.

19. The apparatus of claim 6 wherein said transmitter unit is operable to enter a low power state from an active state in response to said condition signal meeting a second criterion.

20. The apparatus of claim 6 wherein said foot support includes a wall defining said cavity therein, said wall including first and second spaced apart wall portions and a third wall portion extending between said first and second wall portions, such that said transmitter unit is held between said first, second, and third wall portions.

21. The apparatus of claim 6 wherein said cavity has a shape operable to cooperate with a complementary shape of at least part of said transmitter unit to facilitate at least part of said transmitter unit being held in said cavity.

22. The apparatus of claim 6 wherein said transmitter unit holder includes a connector operable to cooperate with a complementary connector on said transmitter unit for holding said transmitter unit in said cavity.

23. The apparatus of claim 6 wherein said transmitter unit further comprises a circuit board.

24. The apparatus of claim 23 wherein said circuit board further comprises a receiver circuit operable to receive configuration information from an external source.

25. The apparatus of claim 24 wherein said configuration information includes a "wake-up" command operable to cause said transmitter unit to enter into an active state from a dormant state.

26. The apparatus of claim 23 wherein said circuit board further comprises a radio frequency circuit mounted on said circuit board and operable to transmit said radio frequency signal.

27. The apparatus of claim 26 wherein said circuit board further comprises a power source mounted on said circuit board and operable to power said radio frequency circuit.

28. The apparatus of claim 27 wherein said power source is a battery.

29. The apparatus of claim 28 further comprising a sidewall including said opening, wherein said battery may be installed from said opening in said sidewall.

30. The apparatus of claim 26 wherein said circuit board further comprises a signal conditioning circuit mounted on said circuit board and operable to facilitate data acquisition from said condition sensor.

31. The apparatus of claim 26 wherein said circuit board further comprises a sampling circuit operable to sample said condition signal at a predetermined rate to determine an amplitude of said condition signal at a plurality of times.

32. The apparatus of claim 31 wherein said circuit board further comprises a format converter circuit for converting an output of said sampling circuit into a predetermined format suitable for transmission by said radio frequency circuit.

33. The apparatus of claim 32 wherein said predetermined format comprises at least one data packet.

34. The apparatus of claim 26 further comprising at least one condition sensor mounted on said foot support.

35. The apparatus of claim 23 wherein said at least one condition sensor is a force sensor.

36. The apparatus of claim 6 further comprising a receiver unit spaced apart from said transmitter unit and operable to receive from said transmitter unit said radio frequency signal representing said condition signal.

37. The apparatus of claim 6 further comprising an article of footwear into which said foot support is inserted.

38. The apparatus of claim 37 wherein said foot support is affixed permanently inside said article of footwear.

39. The apparatus of claim 6 wherein said foot support comprises an insole.

40. The apparatus of claim 6 wherein said transmitter unit is configured to occupy a generally wedge-shaped volume having a shape that is complementary to said cavity of said transmitter unit holder.

41. An apparatus for communicating to a remote location a representation of a physical condition caused by a foot, the apparatus comprising:
    foot support means for supporting a foot, said foot support means being operable to be inserted into footwear and having transmitter holding means including a cavity for holding a transmitter means and said foot support means having an opening in communication with said cavity for removably receiving a battery for powering said transmitter means; and
    transmitter means held by said transmitter holding means, for transmitting a radio frequency signal, said transmitter means being operable to receive from a condition sensor a condition signal representing the physical condition caused by the foot, and to transmit from said transmitter holding means said radio frequency signal representing said condition signal, for reception by a receiver means spaced apart from said transmitter means;
    wherein said cavity has a tapering thickness, being relatively thicker in a medial direction toward a medial side of the foot support and relatively thinner in a lateral direction toward a lateral side of the foot support, said battery being received in the thickest portion of said cavity wherein said thickest portion of said cavity is configured to be located subjacent a medial longitudinal arch of the foot, said thickness being measured in a direction perpendicular to both a longitudinal axis and a transverse axis of said foot support.

42. The apparatus of claim 41 wherein said transmitter means has a shape that is generally complementary to that of said cavity.

43. An apparatus for communicating to a remote location a representation of a physical condition caused by a foot acting on a condition sensor, the apparatus comprising:
    a foot support operable to be inserted into footwear;
    a transmitter unit formed within a transmitter unit holder of increasing thickness between a lateral side of said foot support and a medial side of said foot support and having a thickest portion in an arch area of said foot support, and operable to receive from the condition sensor a condition signal representing the physical condition caused by the foot, said transmitter unit being operable to transmit from said arch area a radio frequency signal representing said condition signal, for reception by a receiver unit spaced apart from said transmitter unit, said transmitter unit comprising:

a circuit board;

a signal conditioning and conversion circuit mounted on said circuit board for conditioning and converting said condition signal into a predetermined format representing said condition signal, said predetermined format being suitable for radio frequency transmission;

a radio frequency circuit mounted on said circuit board and operable to use said predetermined format to transmit said radio frequency signal; and a battery, removably mounted on said circuit board, and operable to power said signal conditioning and conversion circuit and said radio frequency circuit.

44. The apparatus of claim 43, wherein said transmitter unit occupies a volume generally complementary in shape to said increasing thickness of said transmit unit holder.

45. The apparatus of claim 43 wherein said arch area has a top portion and a bottom portion, said transmitter unit holder being located in said bottom portion.

46. An apparatus for communicating to a remote location a representation of a physical condition caused by a foot, the apparatus comprising:

a foot support operable to be inserted into footwear, said foot support having a transmitter unit holder including a cavity operable to hold a transmitter unit; and a transmitter unit in said transmitter unit holder and operable to receive from a condition sensor a condition signal representing the physical condition caused by the foot, said transmitter unit being operable to transmit from said transmitter unit holder a radio frequency signal representing said condition signal, for reception by a receiver unit spaced apart from said transmitter unit;

wherein the cavity has an increasing thickness as it approaches a medial side of said foot support such that the thickest portion of said cavity is adjacent said medial side, said thickness being defined as a measurement along a direction which is perpendicular both to a longitudinal axis and a transverse axis of the foot support.

47. The apparatus of claim 46 wherein said cavity is located in an arch support portion of said foot support, such that when said foot support is used in footwear worn by the foot, the thickest portion of said cavity is located subjacent a medial longitudinal arch of the foot.

48. The apparatus of claim 47 wherein said cavity comprises first and second spaced apart wall portions, a third wall portion extending between the first and second wall portions, and a fourth wall portion, spaced apart from the third wall portion, said first and second wall portions tapering between said third and fourth wall portions to define a decreasing thickness of said cavity in a lateral direction when proceeding from said third wall portion to said fourth wall portion.

49. The apparatus of claim 48 wherein said cavity further comprises a fifth wall portion cooperating with said first, second, third and fourth wall portions, to form said cavity as wedge-shaped, said fifth wall portion becoming gradually closer to a floor of said footwear as said fifth wall portion proceeds from said third wall portion to said fourth wall portion.

50. The apparatus of claim 47 wherein said cavity extends in a lateral direction from a medial midfoot portion of said foot support to about half way across to a lateral midfoot portion of said foot support.

51. The apparatus of claim 47 wherein said cavity extends in a lateral direction from a medial midfoot portion of said foot support to less than half way across to a lateral midfoot portion of said foot support.

52. The apparatus of claim 48 wherein said foot support has an opening in said third wall portion in communication with said cavity for removably inserting a power source into said cavity.

53. The apparatus of claim 46 wherein said transmitter unit has a shape that is generally complementary to that of said cavity.

54. A method of communicating to a remote location a representation of a physical condition caused by a foot, the method comprising:

communicating a condition signal representing the physical condition sensed by a condition sensor to a transmitter unit held within an increasing thickness cavity of said foot support wherein the thickest portion of the cavity is in an arch support portion and towards a medial side of the foot support, said thickness being defined as a measurement along a direction perpendicular to both a longitudinal axis and a transverse axis of the foot support; and transmitting from said transmitter unit a radio frequency signal representing said condition signal, for reception by a receiver unit spaced apart from said transmitter unit.

55. The method of claim 54 wherein the transmitter unit has a shape that is generally complementary to said increasing thickness cavity.

56. A sensing apparatus for insertion into footwear, comprising:

a foot support operable to be inserted into footwear so as to be disposed substantially beneath a foot inserted into the footwear, to retrofit the footwear for sensing a physical condition caused by the foot, said foot support having a top portion and a bottom portion, said top portion being shaped to conform to a sole of the foot, and said bottom portion being shaped to conform to an inner floor of the footwear, said foot support having a transmitter unit holder including a cavity located in an arch support portion of the foot support, said transmitter unit holder being operable to hold a transmitter unit for communicating a representation of the physical condition to a remote location;

said transmitter unit being held in said transmitter unit holder, said transmitter unit operable to receive from a condition sensor a condition signal representing the physical condition caused by the foot, and operable to transmit from said transmitter unit holder a signal representing said condition signal, to a receiver unit at the remote location;

said transmitter unit occupying a generally wedge-shaped volume complementary in shape to the cavity, wherein the cavity has a thickness decreasing from a first thickness at a first location towards a medial side of said arch support portion, to a second thickness at a second location towards a lateral side of said arch support portion, said second thickness being less than said first thickness, such that the cavity is generally wedge-shaped and its location of greatest thickness is configured to be located subjacent a medial longitudinal arch of the foot when said foot support is used in said footwear, wherein said thickness is defined along a direction perpendicular to both a longitudinal axis and a transverse axis of the foot support.

57. The apparatus of claim 56 wherein said footwear comprises an athletic shoe.

58. The apparatus of claim 56 wherein the cavity extends in a lateral direction from said medial side to about half way across a midfoot portion of the foot support.

59. The apparatus of claim 56 wherein the cavity extends in a lateral direction from said medial side to less than half way across a midfoot portion of the foot support.

60. The apparatus of claim 56 wherein the foot support includes an opening in communication with the cavity, wherein the transmitter unit further comprises a circuit board and a battery removably mounted on said circuit board, and wherein said circuit board is configured to position said battery in said cavity adjacent said opening to facilitate said battery being removed and replaced.

61. A foot support apparatus, comprising:
a foot support for insertion into footwear, said foot support having a transmitter unit holder including a cavity in an arch support portion of the foot support, said cavity configured to hold a generally wedge-shaped transmitter unit for receiving from a condition sensor a condition signal representing a physical condition caused by a foot and transmitting a signal representing said condition signal to a receiver unit spaced apart from said transmitter unit;
wherein the cavity is configured to have a thickness tapering from a relatively thick portion in a medial midfoot portion of the foot support to a relatively thinner portion towards a lateral midfoot portion of the foot support, such that the cavity is generally wedge-shaped, said thickness being defined along a direction which is perpendicular both to a longitudinal axis and a transverse axis of the foot support.

\* \* \* \* \*

UNITED STATES PATENT AND TRADEMARK OFFICE
CERTIFICATE OF CORRECTION

PATENT NO. : 7,758,523 B2  Page 1 of 1
APPLICATION NO. : 10/853469
DATED : July 20, 2010
INVENTOR(S) : Timothy Collings et al.

It is certified that error appears in the above-identified patent and that said Letters Patent is hereby corrected as shown below:

In claim 35, at Column 14, Line 13, "claim 23" should be changed to --claim 34--

Signed and Sealed this

Twenty-third Day of November, 2010

David J. Kappos
*Director of the United States Patent and Trademark Office*